US012558041B2

(12) United States Patent
Knodt et al.

(10) Patent No.: US 12,558,041 B2
(45) Date of Patent: Feb. 24, 2026

(54) COUCHTOP BOARD OVERLAY FOR A PATIENT COUCHTOP BOARD AND PATIENT POSITIONING DEVICE

(71) Applicant: Siemens Healthineers AG, Forchheim (DE)

(72) Inventors: Konstantin Knodt, Erbendorf (DE); Ralf Gaertner, Kemnath (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 297 days.

(21) Appl. No.: 18/321,041

(22) Filed: May 22, 2023

(65) Prior Publication Data

US 2023/0371907 A1     Nov. 23, 2023

(30) Foreign Application Priority Data

May 23, 2022    (DE) ..................... 10 2022 205 106.8

(51) Int. Cl.
*A61B 6/04*        (2006.01)
*A61G 13/02*       (2006.01)
*A61N 5/10*        (2006.01)

(52) U.S. Cl.
CPC ............... *A61B 6/04* (2013.01); *A61G 13/02* (2013.01); *A61N 5/1069* (2013.01)

(58) Field of Classification Search
CPC .. A61B 6/04; A61B 6/00; A61G 13/02; A61N 5/1069
USPC .......................................................... 5/601
See application file for complete search history.

(56) References Cited

U.S. PATENT DOCUMENTS

| | | | | |
|---|---|---|---|---|
| 6,895,617 B2 * | 5/2005 | Zacharopoulos | ........ | A61N 5/10 |
| | | | | 5/601 |
| 2011/0173753 A1 * | 7/2011 | Luginbuhl | ............. | A61B 5/055 |
| | | | | 5/601 |
| 2013/0025054 A1 * | 1/2013 | Graw | ................... | A61B 6/0407 |
| | | | | 5/81.1 R |
| 2021/0177362 A1 * | 6/2021 | Filiberti | ............... | A61B 6/0407 |

FOREIGN PATENT DOCUMENTS

| | | | | |
|---|---|---|---|---|
| DE | 2394412 A * | 8/2003 | ............... | A61G 1/00 |
| DE | 202008016701 U1 | 4/2010 | | |
| DE | 202018003540 U1 | 9/2018 | | |

* cited by examiner

*Primary Examiner* — David R Hare
*Assistant Examiner* — Joseane E. Tejada
(74) *Attorney, Agent, or Firm* — Harness, Dickey & Pierce, P.L.C.

(57)        ABSTRACT

A couchtop board overlay for a patient couchtop board extends along a longitudinal direction from a first end section to a second end section. The couchtop board overlay includes a first countercoupling interface in the first end section, wherein, in a state coupled to the first coupling interface, the first countercoupling interface is configured to transmit an application of force in the longitudinal direction onto the couchtop board overlay. The couchtop board overlay further includes a second countercoupling interface in the second end section, wherein, in a coupled state, the second countercoupling interface is connected to the second coupling interface in at least one of a positive-locking or a force-fitted manner.

20 Claims, 4 Drawing Sheets

COUCHTOP BOARD OVERLAY FOR A PATIENT COUCHTOP BOARD AND PATIENT POSITIONING DEVICE

CROSS-REFERENCE TO RELATED APPLICATION(S)

The present application claims priority under 35 U.S.C. § 119 to German Patent Application No. 10 2022 205 106.8, filed May 23, 2022, the entire contents of which are incorporated herein by reference.

BACKGROUND

A couchtop board overlay of this kind is a constituent part of patient positioning devices. Patient positioning devices, for example in the form of a patient couch, are used to position a patient in the course of a magnetic resonance tomography imaging (MRT imaging), a computed tomography imaging (CT imaging), a positron-emission tomography imaging (PET imaging) and/or an irradiation. The material of the patient positioning device must not be visible in the imaging. On the other hand, the material must be sufficiently stable to be able to support the weight of the patient.

By way of the patient positioning device it is possible for example to move a patient before and/or during the performance of the imaging method and/or the irradiation. In order to permit safe movement of the patient and to avoid deformations during the imaging and/or irradiation, it is necessary for the patient positioning device to possess sufficient mechanical stability.

A crucial aspect in tomography applications (for example CT or MRT) is that the deflection of the couchtop board is kept to an absolute minimum. First and foremost it is important that the vertical position of a point on the couchtop board (on which for example the head is situated) varies as little as possible when entering and exiting the field of view (FoV). If this vertical position at the beginning of the FoV deviates too much from that at the end of the FoV, streaks etc. may be produced in the CT image.

Furthermore, couchtop boards for tomography applications are in most cases arcuate in the transverse direction on the top side. Couchtop boards used in radiotherapy planning are level on the top side. Planning the radiotherapy based on a curved couchtop board can result in the region that is to be irradiated being located at a different position during the actual radiotherapy.

For this purpose it has hitherto been provided to keep the deflection to an absolute minimum via a maximally stiff mechanical construction of the couch and the couchtop board. However, greater use of material for the couchtop board leads to an increase in signal attenuation, for example attenuation of the X-ray beam. There are therefore limits to this solution.

SUMMARY

In methods such as computed tomography or for molecular imaging methods such as positron-emission tomography (PET), double-shell couchtop boards have previously been used in most cases in order to produce sufficient stiffness. In a design of said type, use is made for example of two shells made of a bow-shaped carbon-fiber-reinforced plastic (CFRP) which enclose a cavity that is filled with polymethacrylimide foam or wood.

In order to enable a stable positioning state to be achieved in the case of maximally thin couchtop boards, it is possible with certain systems to employ for example a curved aluminum couchtop board which, when moved into an imaging apparatus for example, is received and supported by a supporting device, also referred to as a rear bed.

To that end, flat overlays, also known as couchtop board overlays, are often superimposed on CT couches having couchtop boards that are arcuate in the transverse direction for the purpose of planning the radiotherapy. The overlay is secured to the couch at the clamping point of the couchtop board. In this case the overlay lies in a floating manner on the couchtop board so that when subject to load no shear stress is transmitted from overlay to couchtop board. The overlay therefore rests freely on the couchtop board. This approach can have negative repercussions on the deflection.

It is therefore an object of one or more example embodiments of the present invention to create a couchtop board overlay which exhibits improved mechanical stability and lower overall deflection. In particular, it is an object of one or more example embodiments of the present invention to provide a patient positioning device which affords an improvement in the quality of the generated images during a medical imaging of the patient and/or permits a more targeted dose application during an irradiation of the patient.

At least this object is achieved via a couchtop board overlay according to one or more example embodiments of the present invention, a couchtop board according to claim 1, and/or a patient positioning device according to claim 8. Advantageous embodiments of the present invention will become apparent from the dependent claims, the description and/or the attached figures.

One or more example embodiments of the present invention relate to a couchtop board overlay for a patient couchtop board. The couchtop board overlay is embodied for positioning a patient, for example by placing the patient onto the couchtop board overlay. The couchtop board overlay is embodied for example for equalizing the patient couchtop board with respect to height, curvature or inclination. The patient couchtop board is embodied for supporting the patient, in particular for positioning the patient therewith, during a medical imaging, in particular a computed tomography or magnetic resonance tomography, in particular during an irradiation. In particular, the patient couchtop board, the couchtop board overlay and/or the patient positioning device are compatible for use in medical imaging, magnetic resonance tomography, computed tomography, positron-emission tomography and/or irradiation. The couchtop board overlay and the patient couchtop board are preferably part of a patient positioning device, for example a couch.

The patient couchtop board is embodied to receive the couchtop board overlay. For example, the patient couchtop board accommodates the couchtop board overlay at least partially in a positive-locking and/or force-fitted manner. For example, the couchtop board overlay rests on the patient couchtop board at least in sections, preferably at least in a head section and a foot section. In particular, the patient couchtop board forms a frame at least in sections, preferably in the head section and/or foot section. The couchtop board overlay is preferably placed onto the patient couchtop board and/or supported by the patient couchtop board.

The couchtop board overlay is embodied in particular as planar. The couchtop board overlay can have a level planar extension; alternatively, the couchtop board overlay has a curved planar extension. The couchtop board overlay is in particular embodied as resistant to bending. For example, the couchtop board overlay is made from a plastic, in particular a sandwich material, or from metal. In a plan view from above, the couchtop board overlay preferably has a substantially rectangular shape.

The couchtop board overlay, in particular also the patient couchtop board, has a first end section and a second end section. The first and the second end section are spaced apart at a distance from each other in a longitudinal direction. Disposed between first and second end section is an intermediate section, also referred to as the central section. The first and the second end section are arranged in the longitudinal direction in the vicinity of the two ends of the couchtop board overlay. In other words, the first end section forms one end of the couchtop board overlay and the second end section forms the opposite end in the longitudinal direction. In particular, a central section is disposed between the first end section and the second end section.

The two end sections and the central section divide the planar extension of the couchtop board overlay into three parts. Preferably, each of the end sections comprises between 5 and 10 percent of the surface area. In particular, the first and the second end section each extend over a maximum of 10 percent of the longitudinal extension.

The patient couchtop board has a first coupling interface and a second coupling interface. The first and the second coupling interface are in particular spaced apart at a distance from each other in the longitudinal direction. The first coupling interface is embodied for coupling to a first countercoupling interface. The second coupling interface is embodied for coupling to a second countercoupling interface. The coupling between first coupling interface and first countercoupling interface and/or between second coupling interface and second countercoupling interface is preferably reversible. The first and the second coupling interface are preferably based on different coupling mechanisms.

The couchtop board overlay has a first countercoupling interface in the first end section. The couchtop board overlay has a second countercoupling interface in the second end section. The first countercoupling interface is embodied for coupling and/or connecting to the first coupling interface. The second countercoupling interface is embodied for connecting and/or coupling to the second coupling interface.

The couchtop board overlay and/or the patient positioning device assume/assumes a coupled or connected state when the first countercoupling interface is coupled or connected to the first coupling interface and the second countercoupling interface is coupled and/or connected to the second coupling interface. The coupled state, in particular the coupling and/or connection of the first coupling interface to the first countercoupling interface and/or of the second coupling interface to the second countercoupling interface, is detachable and/or reversible. The coupling and/or connection of first countercoupling interface and first coupling interface is for example a tensile connection, a shear connection, a hook-and-eye connection, a positive-locking and/or a force-fitted connection.

In the coupled state, the first coupling interface applies and/or transmits a force to and/or via the first countercoupling interface. In other words, the first countercoupling interface is subjected to a force, in particular a tensile force and/or a tensioning force, as a result of the coupling to the first coupling interface. The force acts in particular in the longitudinal direction, in particular with an orientation from second end section to first end section. The force, in particular the tensile force and/or tensioning force, acts through the first countercoupling interface on the couchtop board overlay, in particular on the first end section of the couchtop board overlay.

As a result of the coupling and/or connection of the second countercoupling interface to the second coupling interface, a positive-locking and/or force fit is produced between couchtop board overlay and patient couchtop board. In other words, in the coupled state the second countercoupling interface is connected in a positive-locking and/or force-fitted manner to the second coupling interface. The coupling between second countercoupling interface and second coupling interface is for example a plug-and-socket connection, a tongue-and-groove connection, a mortise-and-tenon connection, a positive-locking connection and/or a force-fitted connection.

The present invention is based on the consideration that a mechanically particularly stable overlay for patient positioning is created as a result of the connection of the couchtop board overlay to the patient couchtop board at the two free ends or the two end sections via the coupling interfaces according to one or more example embodiments of the present invention. In particular, one or more example embodiments of the present invention take advantage, in particular via the two couplings, of what is termed the fin-ray effect, which counteracts an excursion movement and/or a local strong deflection. In particular, a substantially constant clearance between couchtop board overlay and patient couchtop board is achieved as a result of the proposed connection, in particular as a result of the two couplings.

It is particularly preferred that the first end section corresponds to a head section and/or forms a head section. The head section is in particular the section and/or end portion of the couchtop board overlay and/or of the patient couchtop board on which and/or in which the head is normally supported and/or which is closest to the head during the positioning of the patient. The second end section is embodied in particular as a foot section and/or corresponds to a foot section. In other words, the second end section corresponds to a portion and/or section of the couchtop board overlay and/or of the patient couchtop board in which the feet are normally arranged and/or which are closest to the feet during the positioning of the patient. In this way it is provided in particular that the first countercoupling interface and/or the first coupling interface are/is arranged in the head section, while the second countercoupling interface and/or the second coupling interface are/is arranged in the foot section. As a result of this embodiment, the couchtop board overlay is connected to the patient couchtop board in a positive-locking and/or force-fitted manner in the foot section, while the couchtop board overlay is connected to the patient couchtop board in a positive-locking and/or force-fitted manner in the head section for the purpose of applying force. In particular, the tensile and/or tensioning force or the force transmission are/is applied in the longitudinal direction in the head section.

It is particularly preferred that the first countercoupling interface is provided as a tensioning interface for transmitting a tensioning and/or tensile force as the force application. In other words, the tensioning interface is embodied to transmit the tensioning and/or tensile force onto the first countercoupling interface or to the couchtop board overlay. In particular, the tensioning interface is embodied to generate and/or transmit an adjustable tensioning and/or tensile force, for example in the form of a pretensioning. In particular, the first coupling interface forms a tensioning interface for coupling to the tensioning interface of the first countercoupling interface. The first countercoupling interface and/or the first coupling interface can for example comprise a tensioning lever, a tensioning mechanism and/or a tensioning spring.

It is particularly preferred that the first coupling interface comprises an eyelet, a loop and/or a hook-up element. In this case the first countercoupling interface has a hook and/or hook-up element. In the coupled state, the hook of the first countercoupling interface is engaged in the eyelet, the loop and/or the first countercoupling interface. In particular, it is also conceivable that the first coupling interface comprises a hook and the first countercoupling interface comprises an eyelet or a loop. The hook is fixed to the couchtop board overlay via a screwed connection, for example.

It is particularly preferred that the second countercoupling interface forms a plug-and-socket connection interface. The second coupling interface in this case forms a counterpiece for the plug-and-socket connection interface. In the coupled state, the couchtop board overlay is connected to the patient couchtop board via the second coupling interface via a plug-and-socket connection and/or is coupled in the form of a plug-and-socket connection. In this case the second coupling interface is embodied in particular for receiving and/or for inserting the second countercoupling interface. In other words, the second countercoupling interface preferably forms a connector for the second coupling interface and/or the second coupling interface preferably forms a female connector, pocket or recess for receiving the second countercoupling interface.

Optionally, it is provided that the second coupling interface has or forms a groove, pocket and/or material recess. The second countercoupling interface in this case comprises and/or forms in particular a spring, a protrusion or a peg. The second coupling interface is in this case embodied to receive the second countercoupling interface, in particular to accommodate it in a positive-locking manner. For example, the second coupling interface forms an edge section of the patient couchtop board, in particular in the second end section. The second countercoupling interface is in particular embodied to receive the edge section and/or a part of the patient couchtop board in a positive-locking manner.

In a possible embodiment of the present invention, it is provided that the first countercoupling interface is arranged on a top side of the couchtop board overlay. The top side of the couchtop board overlay is in particular the side of the planar couchtop board overlay on which the patient is positioned or placed. The second countercoupling interface is preferably arranged on an underside of the couchtop board overlay, the underside being in particular the side of the couchtop board overlay that faces toward the patient couchtop board in the coupled state.

A further subject matter of embodiments of the present invention is formed by a patient positioning device. The patient positioning device is in particular embodied to support, in particular to position and/or move, a patient for the medical imaging and/or irradiation. The patient positioning device comprises or forms a patient couch, for example. The patient positioning device comprises a patient couchtop board overlay according to one or more example embodiments of the present invention, as described hereinabove. With the patient couchtop board in the coupled state, the couchtop board overlay is connected and/or coupled to the first countercoupling interface via the first coupling interface. Further, in the coupled state the couchtop board overlay is connected and/or coupled in a force-fitted and/or positive-locking manner to the patient couchtop board via the second coupling interface and the second countercoupling interface. In particular, in the coupled state the couchtop board overlay is subjected to a force acting in the longitudinal direction, in particular a tensioning force and/or a tensile force. The force-fitted and/or positive-locking connection or coupling of second coupling interface to second countercoupling interface produces in particular a substantially equidistant spacing.

The patient positioning device, in particular the patient couchtop board, optionally comprises a connection module. The connection module in particular comprises the first coupling interface. The patient couchtop board has a couchtop section. The couchtop section is in particular a planar section, in particular a section which is located at the top. The couchtop section is for example the section on which the patient can be positioned when the patient couchtop board is used without the couchtop board overlay. In other words, the couchtop section forms a couch surface.

The connection module is connected in a positive-locking manner to the patient couchtop board, in particular in the couchtop section, in particular in a positive-locking manner. Preferably, the connection module is attached to the patient couchtop board via a screwed connection. The connection module is preferably embodied as block-shaped, cuboidal and/or solid. For example, the connection module comprises a plastic block in order to realize a particularly solid, robust and/or stable construction. In particular, the connection module is arranged in the vicinity of the first end section and/or the head section. The connection module preferably comprises the first coupling interface. This enables the patient couchtop board to be used for positioning the patient without the connection module and to be provided with the first coupling interface by connection to the connection module so that the couchtop board overlay can be used according to one or more example embodiments of the present invention.

It is furthermore particularly preferred that the patient positioning device comprises a clamping plate module. The clamping plate module is embodied as planar. Preferably, the clamping plate module is embodied as resistant to bending, for example as an aluminum, steel, plastic or sheet metal plate. The clamping plate module is preferably embodied at least in sections as congruent with a portion of the couchtop section. The clamping plate module comprises a clamping portion and a stiffening portion. The clamping portion is in particular an end section of the planar clamping plate module. In the coupled state, the clamping portion is arranged or clamped in place between the couchtop section, or the patient couchtop board, and the connection module. In other words, via a positive-locking connection of the connection module to the couchtop section or the patient couchtop board, the clamping portion of the clamping plate module is clamped in place therebetween in a force-fitted and/or positive-locking manner. In particular, as a result of the screwed or positive-locking connection of the connection module to the patient couchtop board, the clamping portion or the clamping plate module is also connected via the screwed connection and/or in a positive-locking manner.

The clamping plate module comprises a stiffening portion, the stiffening portion being embodied at least in sections as planar. In the stiffening portion, the clamping plate module is connected to the couchtop section or the patient couchtop board in a positive-locking manner. In the stiffening portion, the clamping plate module is preferably fixed to the couchtop section or the patient couchtop board via a screwed connection. The stiffening portion is embodied to stiffen and/or mechanically stabilize the couchtop section.

It is optionally provided that the first coupling interface comprises a pretensioning unit. For example, the pretensioning unit comprises a pretensioning lever or a rotatory element for setting a pretension, the tensile force, the tensioning force and/or the force application. In the coupled state, the pretensioning unit is embodied to apply an adjustable pretension, for example a tensile force or tensioning force, to the first countercoupling interface. In other words, the tensile force and/or tensioning force that acts on the first countercoupling interface or on the couchtop board overlay can be set via the pretensioning unit.

The patient couchtop board and/or the couchtop section comprise/comprises in particular a second foot section. The second foot section is spaced apart at a distance from a second head section of the patient couchtop board in the longitudinal direction. A free end and/or edge section of the second foot section preferably form/forms the second coupling interface. In other words, the second foot section and/or the edge section form/forms a spring, a peg and/or collar for being received in a positive-locking manner by the second coupling interface, in particular in the form of a groove or pocket. The second countercoupling interface, in particular the recess, groove or pocket, accommodates the free end of the second foot section at least in sections in a positive-locking manner. The positive-locking connection between couchtop board overlay and patient couchtop board can be realized in a particularly simple and stable manner in this way as a result of the foot section being accommodated in a pocket, groove or recess.

It is particularly preferred that the couchtop section, in particular the patient couchtop board, is concavely curved in a transverse direction orthogonal to the longitudinal direction, the couchtop board overlay preferably being embodied as level and/or uncurved. In other words, the couchtop board overlay is embodied to reconfigure a curved, in particular concavely curved, couchtop section of a patient couchtop board into a level couch surface in order thereby to position the patient for irradiation, for example. This permits a patient couchtop board, which is often embodied as curved for imaging purposes, to be able to be employed for irradiation purposes via the couchtop board overlay.

The patient positioning device, in particular the coupled state of patient couchtop board and couchtop board overlay, is based on and/or realizes in particular the fin-ray effect, with the result that the patient positioning device counteracts an excessive deflection of the couchtop section. The fin-ray effect is produced in particular as a result of the positive-locking and/or force-fitted coupling of couchtop board overlay and patient couchtop board in the first and second end section.

It is particularly preferred that the couchtop board overlay and/or the patient couchtop board are/is made from a fiber composite material, in particular a carbon-fiber-reinforced plastic (CFRP). This allows the couchtop board to have the lowest possible aluminum equivalent value and consequently to exert a minimal influence on the imaging.

BRIEF DESCRIPTION OF THE DRAWINGS

Further advantages, effects and embodiments will become apparent from the attached figures and their description. In the figures.

DETAILED DESCRIPTION

Figure 1:
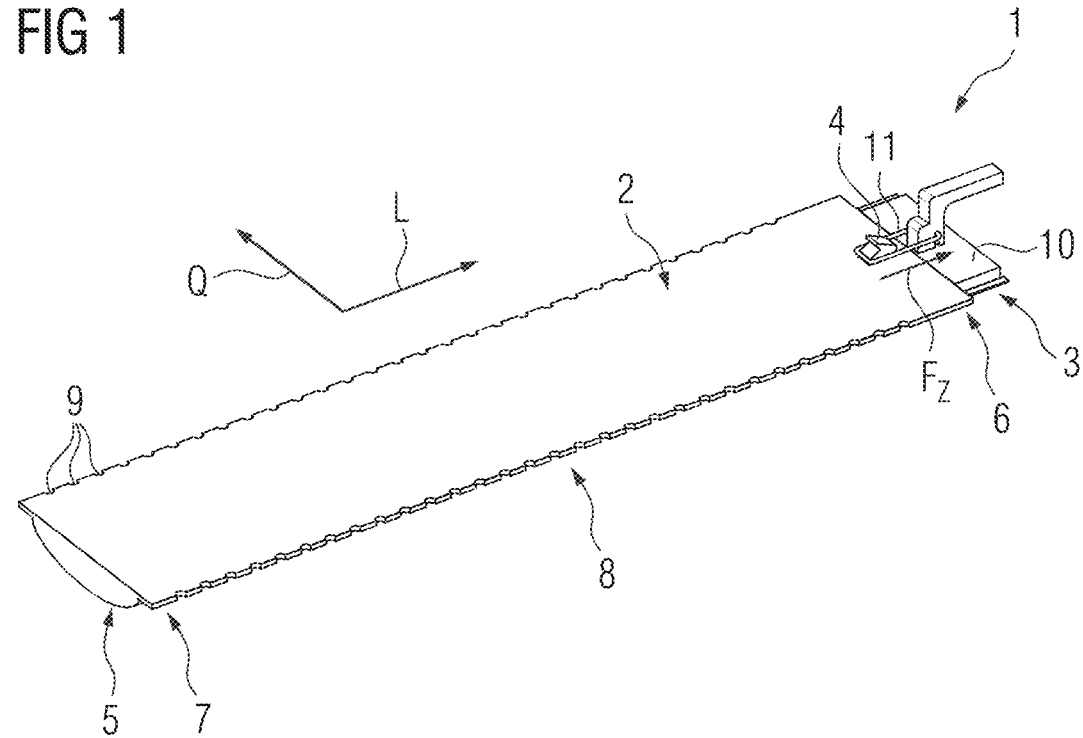
FIG. 1 shows an exemplary embodiment of a patient positioning device.

FIG. 1 shows an exemplary embodiment of a patient positioning device 1. The patient positioning device 1 is embodied for example as a couch or forms a part of a couch for positioning a patient. The patient positioning device 1 is used for example in the course of the imaging examination of a patient via computed tomography or magnetic resonance tomography. Furthermore, the patient positioning device 1 is used for positioning the patient during irradiation in the course of a tumor treatment. The patient positioning device 1 is in particular a mobile, for example maneuverable, patient couch.

The patient positioning device 1 comprises a couchtop board overlay 2 and a patient couchtop board 3. The patient positioning device 1 without the couchtop board overlay 2, in other words the patient couchtop board 3, is used for example for positioning a patient during the medical imaging since the patient is often positioned on a convexly curved couch surface during this process. For irradiation, on the other hand, the patient is positioned on a level couch surface, the medical imaging for irradiation planning likewise being performed with the patient positioned on a level surface. A patient couchtop board 3 having a curved couch surface can be modified for use in an irradiation process by mounting, in particular coupling, the couchtop board overlay 3 to or with the patient couchtop board 3. The couchtop board overlay 2 is coupled or connected to the patient couchtop board 3 via a first countercoupling interface 4 and a second countercoupling interface 5. This coupling or connection is a reversible and/or detachable coupling/connection.

In a plan view from above, the couchtop board overlay 2 is embodied as rectangular. The couchtop board overlay 2 extends in a longitudinal direction L by at least 1.8 m. In a transverse direction Q, the couchtop board overlay 2 extends to at least 60 cm, which is also referred to as the width. The couchtop board overlay 2 is embodied as planar, in particular planar in the longitudinal direction L and the transverse direction Q. The couchtop board overlay 2 is embodied for example as plate- or board-shaped and has a thickness or material thickness of less than 5 cm.

The couchtop board overlay 2 comprises a first end section 6, a second end section 7 and an intermediate section, also referred to as the central section 8. The two end sections 6, 7 are defined in particular by the ends of the planar couchtop board overlay 2 that are spaced apart at a distance from each other in the longitudinal direction L, the central section 8 lying between the two end sections 6, 7. In the longitudinal direction L, the couchtop board overlay 2 has index markers 9 which can be used for positioning the patient during the imaging or during the irradiation.

The patient positioning device 1 comprises a connection module 10 which is connected to the patient couchtop board 3 in a positive-locking manner. The connection module 10 comprises a first coupling interface 11 which is embodied for coupling to the first countercoupling interface 4. As a result of the coupling of the first countercoupling interface 4 to the first coupling interface 11, a tensile force Fz is transmitted to the couchtop board overlay 2, in particular to the first end section 6, which tensile force Fz acts in the longitudinal direction L.

Figure 2:
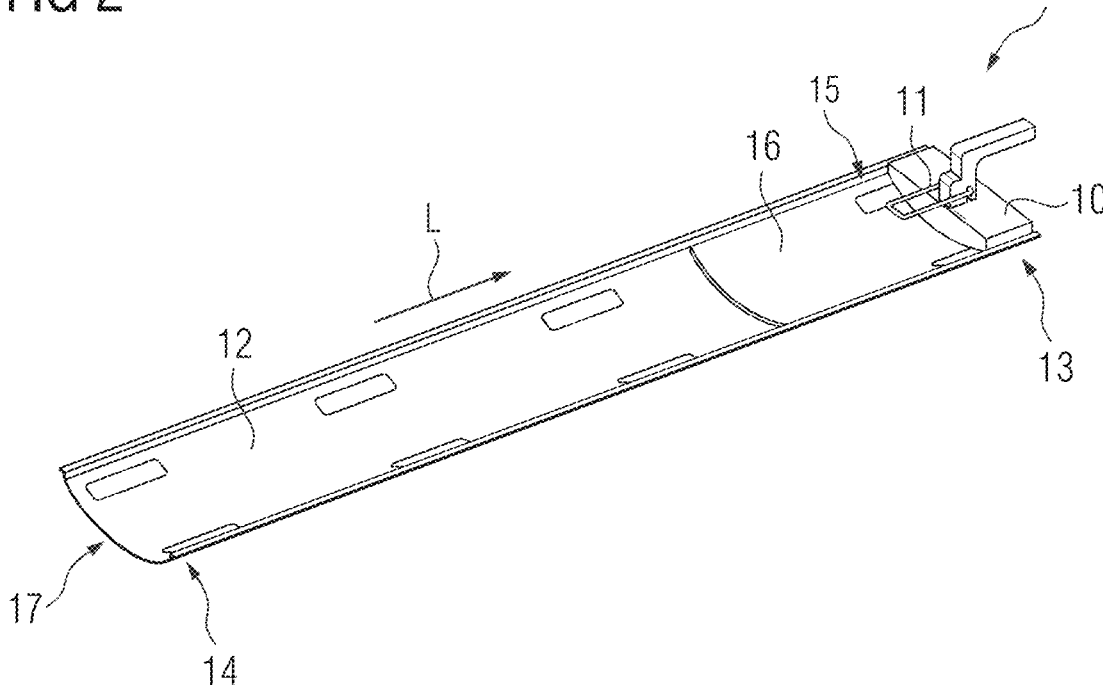
FIG. 2 shows an exemplary embodiment of a patient couchtop board.

FIG. 2 shows an exemplary embodiment of the patient couchtop board 3. The patient couchtop board 3 comprises a couchtop section 12 which is convexly curved and which is embodied for positioning the patient. For example, the patient couchtop board 3, in particular the couchtop section 12, is embodied as a half-shell. The patient couchtop board 3 extends in the longitudinal direction L and has a first end 13 and a second end 14. The second end 14 is preferably arranged in the foot section. The free second end 14 forms the second countercoupling interface 5, which can be inserted into a pocket and thus engages in a plug-and-socket connection.

The patient couchtop board 3 is connected to the connection module 10 and/or comprises the latter. In this case the connection module 10 forms a fixing block. The connection module 10 comprises the first coupling interface 11, which is embodied as a tensioning lever and/or comprises the same. The coupling interface 11 comprises an eyelet. In this case the first countercoupling interface 4 comprises a hook which can engage in the eyelet. Tensile force FZ applied to the hook via the eyelet can be set via the tensioning lever. The connection module 10 is fixed to the patient couchtop board 3 via a screwed connection.

A clamping plate module 15 is arranged between the connection module 10 and the patient couchtop board 3 or the couchtop section 12. The clamping plate module 15 comprises a clamping portion and a stiffening portion 16. The clamping portion is arranged and/or clamped in place between the couchtop section 12 and the connection module 10. The stiffening portion 16 extends in the longitudinal direction from the first end 13 to the second end 14. The stiffening portion 16 is embodied as planar and in particular congruent with a subsection of the couchtop section 12. In the stiffening portion 16, the clamping plate module 15 is fixed to the couchtop section 12 via a screwed connection and thus provides an enhanced mechanical stability.

Figure 3:
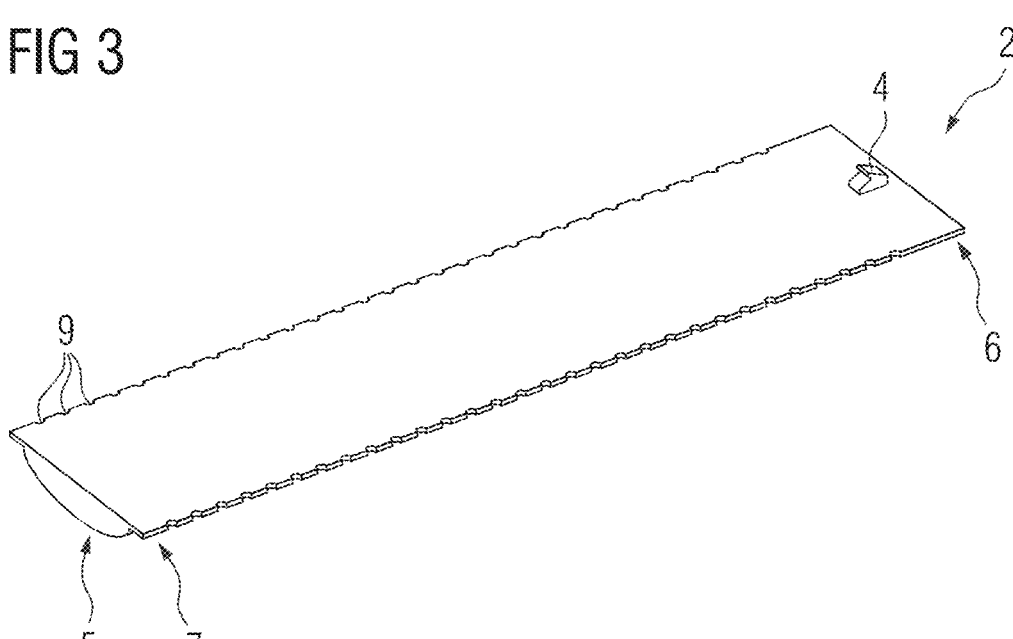
FIG. 3 shows an exemplary embodiment of a couchtop board overlay.

FIG. 3 shows the couchtop board overlay 2 from FIG. 1. The couchtop board overlay 2 comprises a hook as a first countercoupling interface 4. The first countercoupling interface 4, in particular the hook, is fixed to the couchtop board overlay 1 via a screwed connection.

Figure 4:
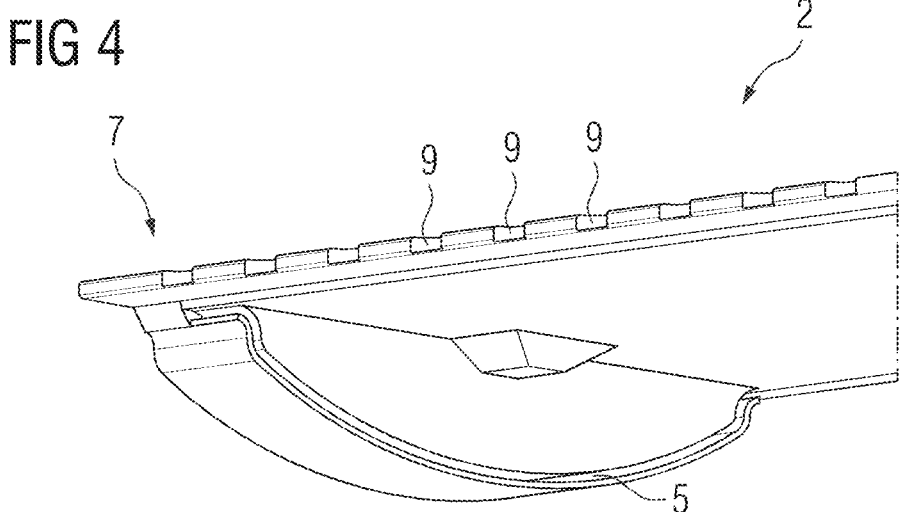
FIG. 4 shows a detailed view of the couchtop board overlay from FIG. 3.

FIG. 4 shows a detailed view of the couchtop board overlay 2 from FIG. 1 or FIG. 3. The couchtop board overlay 2 comprises a pocket on an underside as the second countercoupling interface 5 as a receptacle for the second coupling interface 17. The pocket of the second countercoupling interface 5 is shaped to match the contour of the second end 14 of the patient couchtop board 3 and in this configuration is embodied as bow-shaped. The bow-shaped embodiment results from the convex curvature of the patient couchtop board 3. The pocket accommodates the second coupling interface 17, in particular the edge of the patient couchtop board 3, in a positive-locking manner. The couchtop board overlay 2 is therefore connected to the patient couchtop board 3 at two points, one connection being realized in the first end section 6 and one connection being realized in the second end section 7.

Figure 5A:
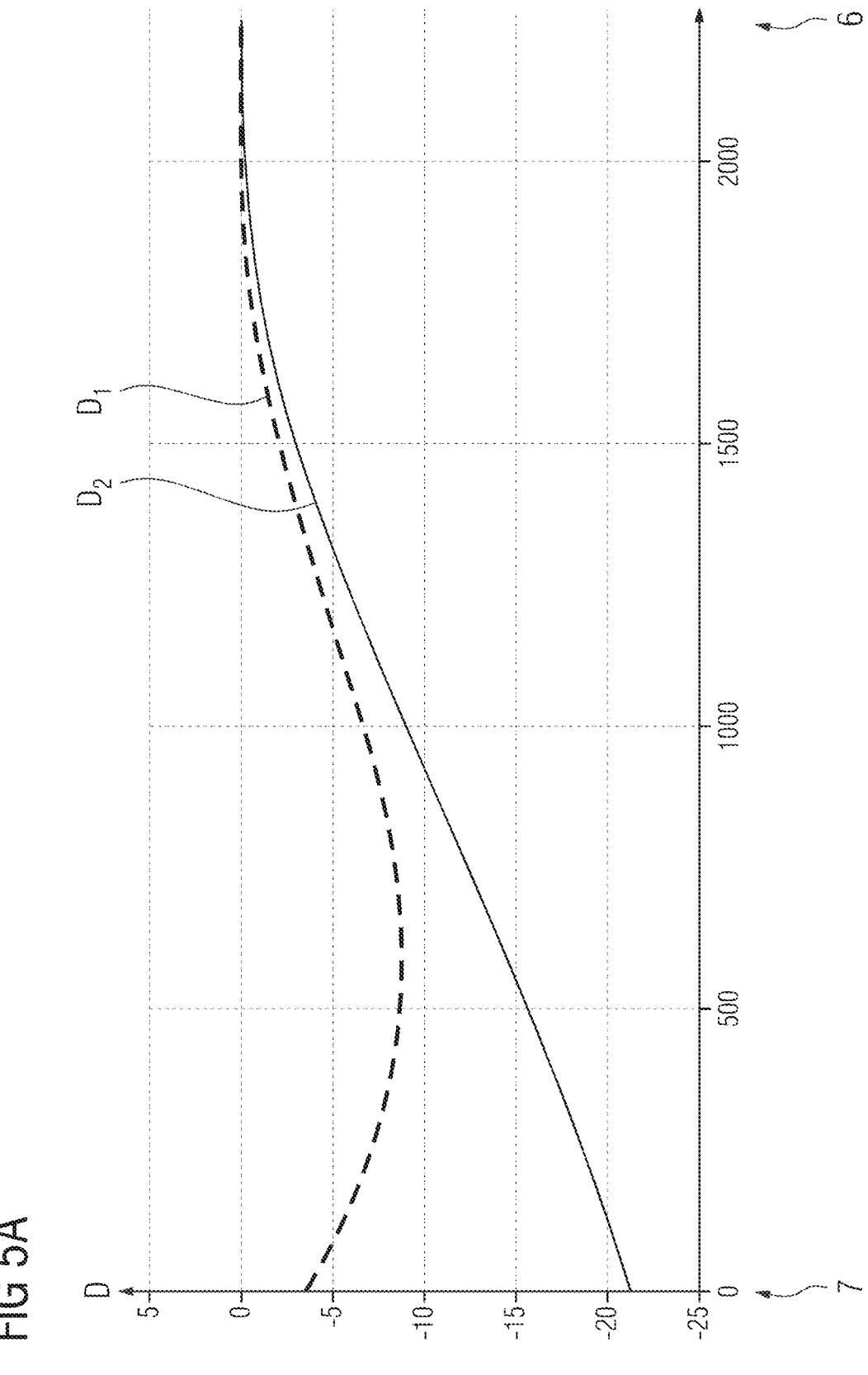
FIGS. 5a, 5b, 5c show FEM simulations of a patient positioning device.

FIGS. 5a, b, c show FEM simulations of the patient positioning device 1. The patient positioning device 1 forms a fin-ray structure. The fin-ray structure is produced in particular as a result of the positive-locking connection in the second end section 6 and the positive-locking connection in the first end section 5. FIG. 5a shows the deflection D1 of the patient positioning device 1 when the connection of the latter is realized, according to an example embodiment of the present invention, via the first and second coupling interfaces 11, 17. It is evident in this case that the deflection remains slight even under severe loading, for example due to a heavy patient. The deflection D2 for a patient positioning device without the two inventive connections or couplings is substantially greater and at a maximum in one of the end sections 6, 7.

Figure 5B:
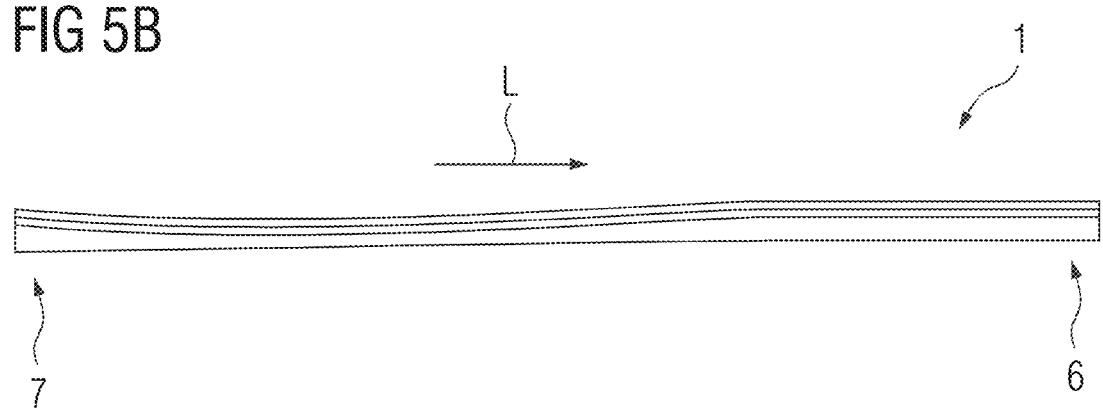
Figure 5C:
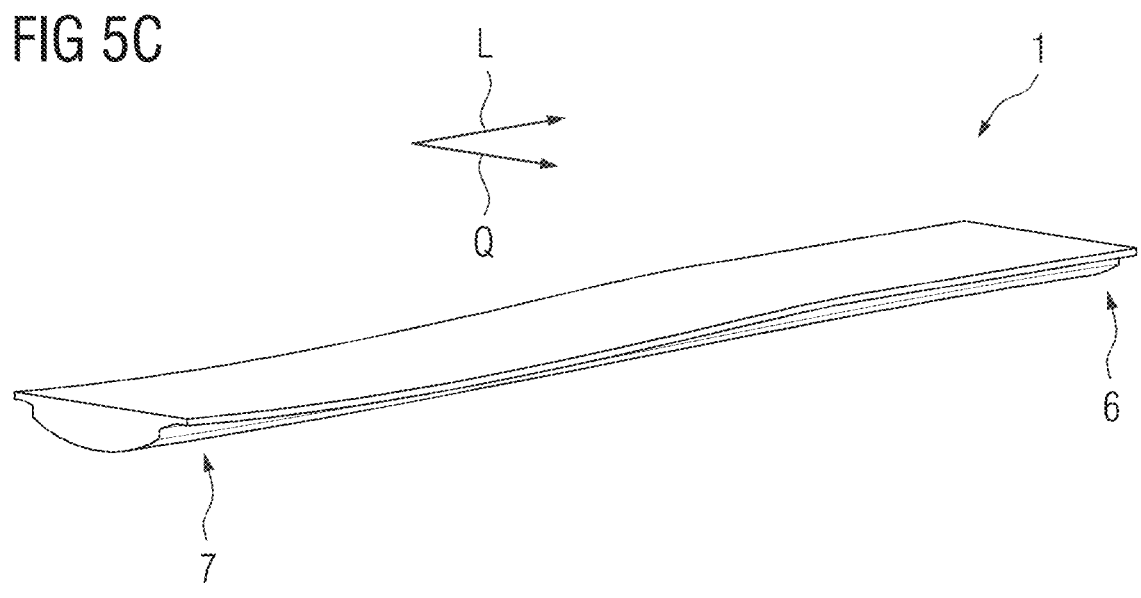

FIG. 5b shows the deformation or compression of the patient positioning device 1 for the support of a heavy patient. In this case there results for the patient positioning device 1, according to an example embodiment of the present invention, a section of maximum deflection which is not arranged at the end sections 5, 6. The distribution of the weight force within the planar extension of the couch surface is shown in FIG. 5c.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A couchtop board overlay for a patient couchtop board for patient positioning for a medical imaging or irradiation apparatus, wherein the patient couchtop board is configured to receive the couchtop board overlay and includes a first coupling interface and a second coupling interface, wherein the couchtop board overlay extends along a longitudinal direction from a first end section to a second end section, and wherein the couchtop board overlay comprises:

a first countercoupling interface in the first end section, the first countercoupling interface being configured to transmit an application of force onto the couchtop board overlay in the longitudinal direction in a state in which the first countercoupling interface is coupled to the first coupling interface; and a second countercoupling interface in the second end section, wherein in a coupled state the second countercoupling interface is connected to the second coupling interface in at least one of a positive-locking or a force-fitted manner.

2. The couchtop board overlay as claimed in claim 1, wherein at least one of (i) the first end section forms a head end section or (ii) the second end section forms a foot end section.

3. The couchtop board overlay as claimed in claim 1, wherein the first countercoupling interface forms a tensioning interface configured to transmit at least one of a tensioning force or a tensile force as the application of force.

4. The couchtop board overlay as claimed in claim 1, wherein the first coupling interface includes an eyelet, and wherein the first countercoupling interface includes a hook configured to engage with the eyelet in the state in which the first countercoupling interface is coupled to the first coupling interface.

5. The couchtop board overlay as claimed in claim 1, wherein the second countercoupling interface forms a plug-and-socket connection interface, and the second countercoupling interface is configured to, in the coupled state, connect the couchtop board overlay to the patient couchtop board via the second coupling interface via a plug-and-socket connection.

6. The couchtop board overlay as claimed in claim 1, wherein the second countercoupling interface comprises at least one of a pocket or a groove configured to receive the second coupling interface.

7. The couchtop board overlay as claimed in claim 1, wherein at least one of (i) the first countercoupling interface is arranged on a top side of the couchtop board overlay or (ii) the second countercoupling interface is arranged on an underside of the couchtop board overlay.

8. A patient positioning device comprising:

a patient couchtop board; and the couchtop board overlay as claimed in claim 1, wherein in a coupled state, the first coupling interface is connected to the first countercoupling interface in at least one of a force-fitted or a positive-locking manner, and in the coupled state, the second coupling interface is connected to the second countercoupling interface in at least one of a force-fitted or a positive-locking manner.

9. The patient positioning device as claimed in claim 8, further comprising:

a connection device including the first coupling interface, wherein the patient couchtop board includes a couchtop section, and the connection device is connected to the couchtop section in a positive-locking manner.

10. The patient positioning device as claimed in claim 8, further comprising:

a clamping plate device, wherein the clamping plate device is planar and includes a clamping portion and a stiffening portion, the clamping portion is arranged between a couchtop section and a connection device, and the clamping plate device is connected to the couchtop section in the stiffening portion in at least one of a positive-locking or a force-fitted manner.

11. The patient positioning device as claimed in claim 8, wherein the first coupling interface includes a pretensioning device configured to subject the first countercoupling interface to at least one of an adjustable pretension, a force application, a tensioning force or a tensile force in the coupled state.

12. The patient positioning device as claimed in claim 9, wherein the couchtop section has a foot section and a head section spaced apart at a distance from each other in the longitudinal direction, wherein a free end of the foot section forms the second coupling interface, wherein the second countercoupling interface has at least one of a material recess, a groove or a pocket, and wherein, in the coupled state, the free end of the foot section is accommodated in a positive-locking manner by at least one of the material recess, the groove or the pocket.

13. The patient positioning device as claimed in claim 9, wherein the couchtop section is concavely curved in a transverse direction orthogonal to the longitudinal direction, and wherein the couchtop board overlay is level for positioning a patient.

14. The patient positioning device as claimed in claim 8, wherein, with the couchtop board overlay in the coupled state, the patient couchtop board forms a fin-ray structure.

15. The patient positioning device as claimed in claim 8, wherein the couchtop board overlay includes a fiber composite material.

16. The couchtop board overlay as claimed in claim 3, wherein the first coupling interface includes an eyelet, and wherein the first countercoupling interface includes a hook configured to engage with the eyelet in the state in which the first countercoupling interface is coupled to the first coupling interface.

17. The couchtop board overlay as claimed in claim 4, wherein the second countercoupling interface forms a plug-and-socket connection interface, and the second countercoupling interface is configured to, in the coupled state, connect the couchtop board overlay to the patient couchtop board via the second coupling interface via a plug-and-socket connection.

18. The couchtop board overlay as claimed in claim 4, wherein the second countercoupling interface comprises at least one of a pocket or a groove configured to receive the second coupling interface.

19. The patient positioning device as claimed in claim 9, wherein the positive-locking manner includes being connected at least one of (i) via a screwed connection or (ii) reversibly.

20. The patient positioning device as claimed in claim 15, wherein the fiber composite material is a carbon-fiber-reinforced plastic.

* * * * *